United States Patent
Li et al.

(10) Patent No.: US 10,004,274 B2
(45) Date of Patent: Jun. 26, 2018

(54) ATOMIZER CAPABLE OF REFILLING TOBACCO LIQUID WITHOUT LEAKING AND ELECTRONIC CIGARETTE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Youli Shen, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 0 days. days.

(21) Appl. No.: 15/438,755

(22) Filed: Feb. 21, 2017

(65) Prior Publication Data

US 2017/0156408 A1 Jun. 8, 2017

(30) Foreign Application Priority Data

Feb. 26, 2016 (CN) .................... 2016 2 0144948 U

(51) Int. Cl.

| A24F 47/00 | (2006.01) |
|---|---|
| A61M 15/06 | (2006.01) |
| H05B 3/16 | (2006.01) |
| A61M 11/04 | (2006.01) |

(52) U.S. Cl.
CPC ......... *A24F 47/008* (2013.01); *A61M 11/042* (2014.02); *A61M 15/06* (2013.01); *H05B 3/16* (2013.01); *A61M 2205/3653* (2013.01); *A61M 2205/8206* (2013.01); *A61M 2209/045* (2013.01); *H05B 2203/014* (2013.01); *H05B 2203/021* (2013.01)

(58) Field of Classification Search
None
See application file for complete search history.

(56) References Cited

U.S. PATENT DOCUMENTS

| 2014/0360514 A1* | 12/2014 | Zhu | ........................ A24F 47/008 |
|---|---|---|---|
| | | | 131/329 |
| 2015/0007836 A1* | 1/2015 | Li | ........................ A24F 47/008 |
| | | | 131/329 |

* cited by examiner

*Primary Examiner* — Tho D Ta
(74) *Attorney, Agent, or Firm* — Cheng-Ju Chiang

(57) ABSTRACT

An atomizer includes a housing assembly, an atomizing core, a lid, a liquid blocking cover, and an elastic element. The housing assembly defines a liquid chamber. The atomizing core is configured for atomizing the tobacco liquid. The lid is configured for sealing the liquid chamber, and is detachable from the housing assembly. The liquid blocking cover is movably arranged in the housing assembly. The elastic element elastically abuts against the liquid blocking cover. When the lid is connected with the liquid blocking cover, the lid is capable of driving the liquid blocking cover to move to a first position where the tobacco liquid in the liquid chamber can flow to the atomizing core. When the lid is detached from the housing assembly, the liquid blocking cover is driven by the elastic element to a second position where the atomizing core is isolated from the liquid chamber.

12 Claims, 6 Drawing Sheets

ATOMIZER CAPABLE OF REFILLING TOBACCO LIQUID WITHOUT LEAKING AND ELECTRONIC CIGARETTE HAVING SAME

TECHNICAL FIELD

The present invention relates to electronic cigarettes, and particularly to an atomizer and an electronic cigarette using same.

BACKGROUND ART

A refillable electronic cigarette is becoming more and more popular because it is environmental-friendly. When tobacco liquid in the refillable electronic cigarette is used up, the user of the electronic cigarette usually uses an injector to fill in tobacco liquid. However, during this process, the tobacco liquid may leak out. For example, since the injector is not fixedly coupled with the electronic cigarette, the tobacco liquid may leak when the electronic cigarette is turned over, thus rendering user experience unsatisfactory.

What are needed, therefore, are an atomizer and an electronic cigarette using same, which can overcome the above shortcomings.

SUMMARY

An atomizer includes a housing assembly, an atomizing core, a lid, a liquid blocking cover, and an elastic element. The housing assembly defines a liquid chamber. The atomizing core is configured for atomizing the tobacco liquid. The lid is configured for sealing the liquid chamber, and is detachable from the housing assembly. The liquid blocking cover is movably arranged in the housing assembly. The elastic element elastically abuts against the liquid blocking cover. When the lid is connected with the liquid blocking cover, the lid is capable of driving the liquid blocking cover to move to a first position where the tobacco liquid in the liquid chamber can flow to the atomizing core. When the lid is detached from the housing assembly, the liquid blocking cover is driven by the elastic element to a second position where the atomizing core is isolated from the liquid chamber.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
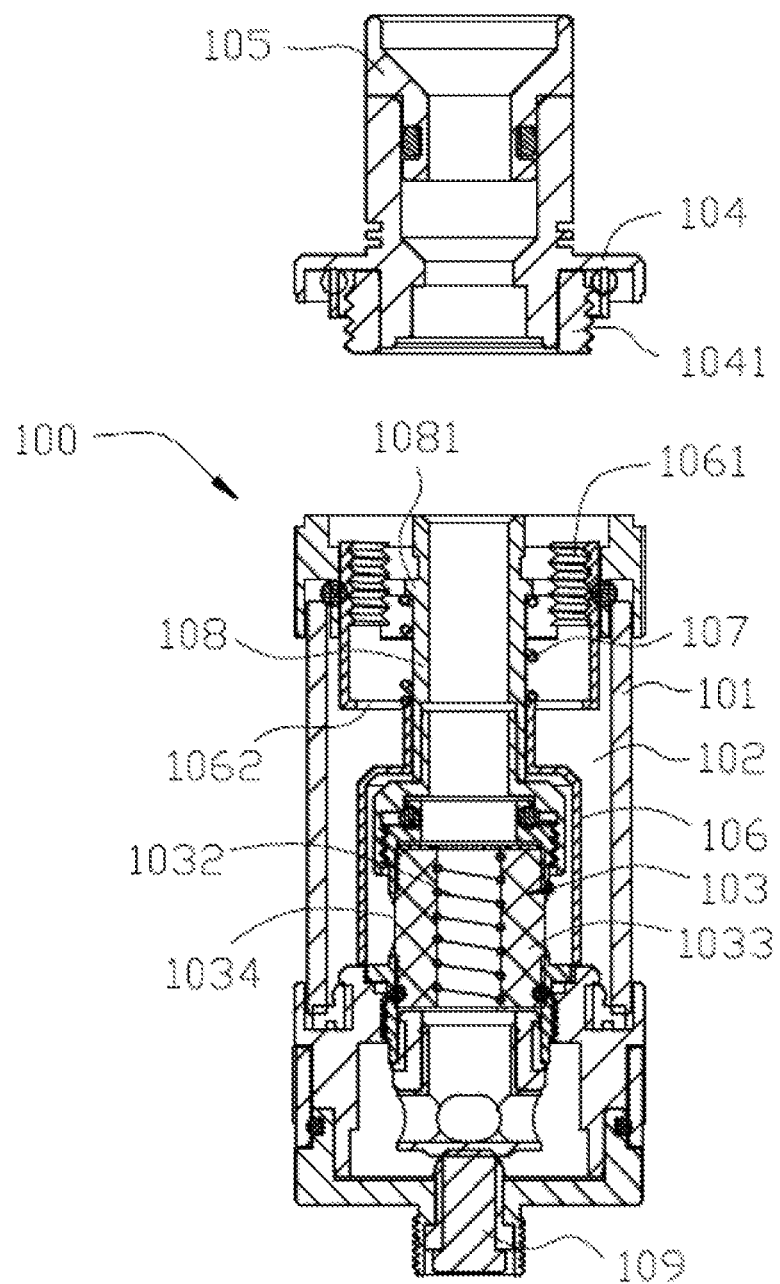
FIG. 1 is a cross-sectional view of an atomizer according to an embodiment including a lid, when the lid is detached.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Referring to FIG. 1, an atomizer 100 is shown. The atomizer 100 includes a housing assembly 101, an atomizing core 103, a liquid blocking cover 106, an elastic element 107, and a lid 104. The atomizing core 103, the liquid blocking cover 106, and the elastic element 107 are arranged in the housing assembly 101. The lid 104 is connected to an end of the housing assembly 101. In the present embodiment, the housing assembly 101 is substantially cylindrical, and defines a liquid chamber 102 for storing tobacco liquid. The lid 104 is configured (i.e., structured and arranged) for sealing the liquid chamber 102. The lid 104 is detachable from the housing assembly 101, so that tobacco liquid can be injected into the liquid chamber 102. Generally, the lid 104 is arranged at a top part of the housing assembly 101, and a mouthpiece 105 is arranged at a top part of the lid 104. The atomizing core 103 is in communication with the mouthpiece 105, and is configured for atomizing the tobacco liquid to form aerosol. The aerosol is expelled via the mouthpiece 105. When the lid 104 and the mouthpiece 105 are detached, tobacco liquid can be injected into the liquid chamber 102 from top thereof.

Figure 2:
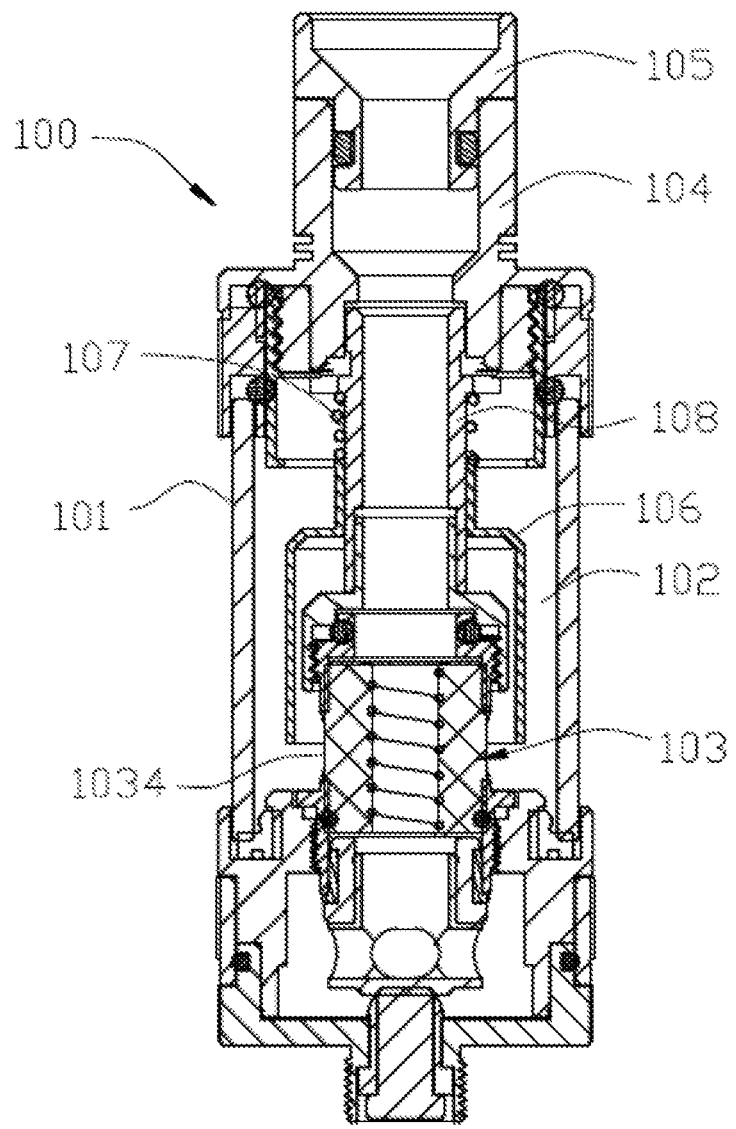
FIG. 2 is an assembled view of the atomizer of FIG. 1.

The liquid blocking cover 106 is movably arranged in the housing assembly 101, and is detachably connected with the lid 104. The atomizing core 103 is separated from the liquid chamber 102 or in communication with the liquid chamber 102 by changing a position of the liquid blocking cover 106. When the lid 104 is connected with the liquid blocking cover 106, the lid 104 drives the liquid blocking cover 106 to move, so that the tobacco liquid in the liquid chamber 102 flows into the atomizing core 103, as seen in FIG. 2. In this state, the atomizing core 103 can work normally. When the lid 104 is detached, tobacco liquid can be injected, and the liquid blocking cover 106 is driven to return to its original position upon an elastic force of the elastic element 107 where the liquid blocking cover 106 separates the liquid chamber 102 from the atomizing core 103. In this state, the tobacco liquid cannot flow into the atomizing core 103, as seen in FIG. 1.

Quite usefully, the lid 104 is rotatably connected to the housing assembly 101, and the lid 104 and the liquid blocking cover 106 are threadedly coupled with each other. The lid 104 includes a threaded part 1041, and the liquid blocking cover 106 includes a corresponding threaded connecting part 1061. The liquid blocking cover 106 is movable along an axial direction of the atomizer 100, and is unable to rotate. Accordingly, when the lid 104 is rotated, the lid 104 drives the liquid blocking cover 106 to move axially.

Referring to FIG. 1 again, the elastic element 107 may be a spring, a first end of the elastic element 107 abuts against a top part of the air pipe 108, and an opposite second end of the elastic element 107 abuts against the liquid blocking cover 106. In a liquid filling state, the lid 104 is disengaged with the liquid blocking cover 106, the elastic element 107 drives the liquid blocking cover 106 to move downwards, a bottom part of the liquid blocking cover 106 is in tight contact with a bottom of the liquid chamber 102. The atomizing core 103 is completely isolated in the liquid blocking cover 106, avoiding liquid leakage from the atomizing core 103 during liquid filling process. In detail, the liquid blocking cover 106 and the housing assembly 101 cooperatively define the liquid chamber 102. The liquid blocking cover 106 further defines a plurality of liquid filling openings 1062. External liquid injecting device can be inserted into the liquid filling openings 1062, so that tobacco liquid can be filled into the liquid chamber 102.

Referring to FIG. 2, when the lid 104 is rotated, the lid 104 is threadedly coupled with the liquid blocking cover 106, the liquid blocking cover 106 is driven to move upwards axially by the lid 104, and the atomizing core 103 is in communication with the liquid chamber 102. In this state, the atomizer 100 can work normally. A sealing ring is provided between the lid 104 and the housing assembly 101. When the lid 104 is rotated in place, the lid 104 seals a top end of the liquid chamber 102.

Figure 3:
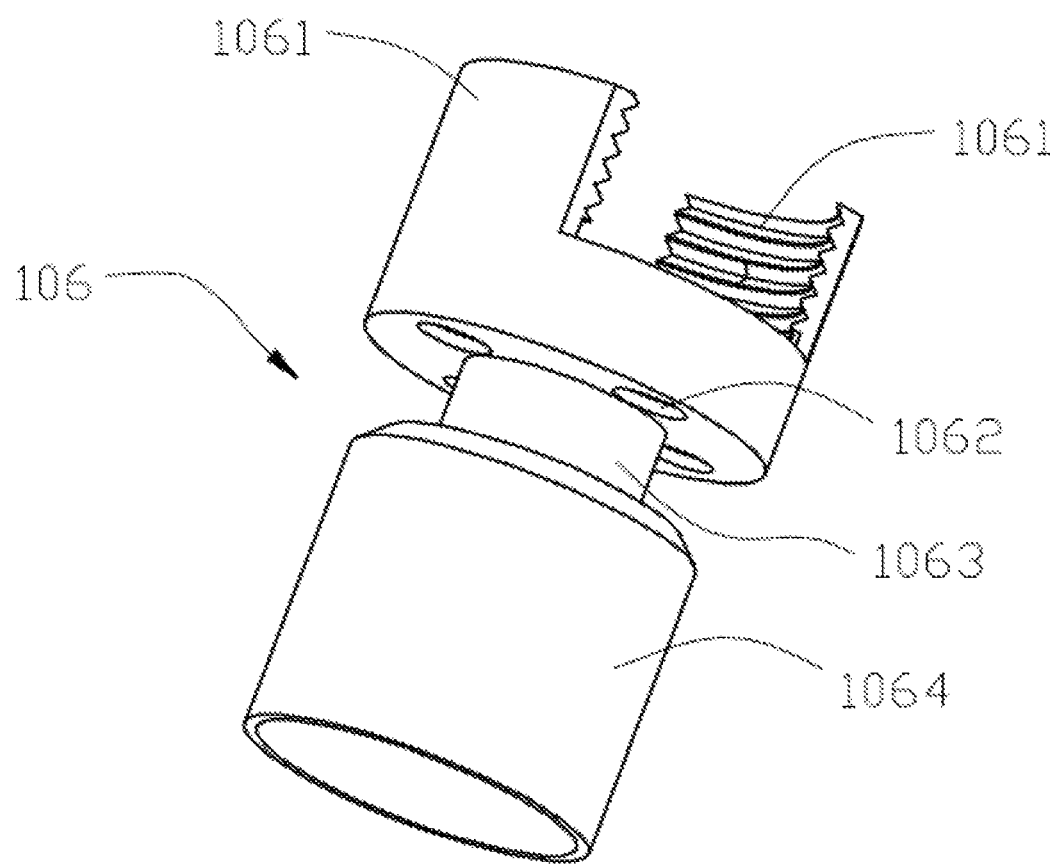
FIG. 3 is a perspective view of a liquid blocking cover of the atomizer of FIG. 1.
Figure 4:
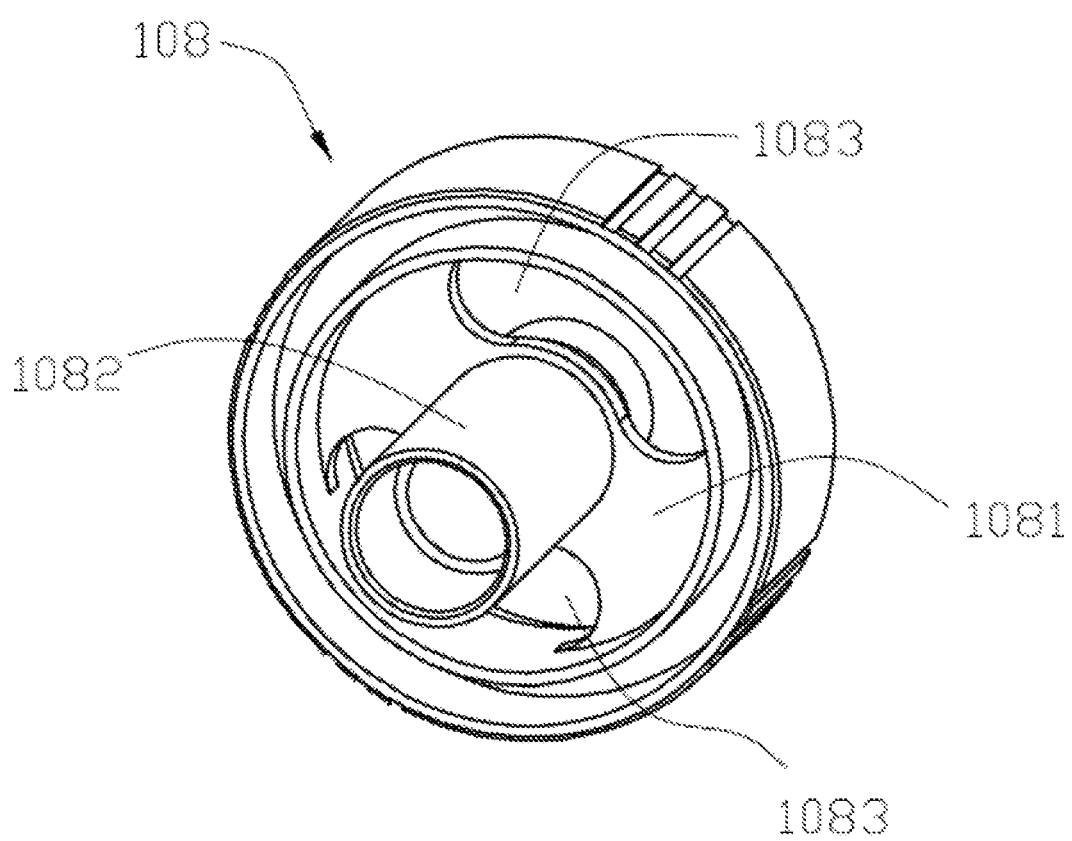
FIG. 4 is a perspective view of an air pipe of the atomizer of FIG. 1.

Referring to FIGS. 1 and 3-4, the air pipe 108 is arranged between the mouthpiece 105 and the atomizing core 103. The air pipe 108 allows aerosol to pass therethrough. The liquid blocking cover 106 nests the air pipe 108, and is slidable along a longitudinal direction along the air pipe 108. The air pipe 108 is configured for guiding the liquid blocking cover 106 to slide. A sealing ring is further provided between the air pipe 108 and the liquid blocking cover 106.

In detail, the liquid blocking cover 106 includes a nesting part 1063, an isolating part 1064, and the threaded connecting part 1061. The nesting part 1063 sleeves the air pipe 108. The isolating part 1064 receives the atomizing core 103. A diameter of the isolating part 1064 is larger than that of the nesting part 1063. A sealing ring is provided between the nesting part 1063 and the air pipe 108. A top part of the nesting part 1063 extends radially to form an annular part, and the liquid filling openings 1062 are evenly define in a bottom part of the annular part. The threaded connecting part 1061 is formed on the annular part. The threaded connecting part 1061 is divided into two pieces. The air pipe 108 includes a pipe body 1082 and an obstructing part 1081 extending radially from the pipe body 1082. The obstructing part 1081 is configured for preventing the liquid blocking cover 106 from rotating when the lid 104 is connected with the liquid blocking cover 106. The obstructing part 1081 defines two through holes 1083, so that the two pieces of the threaded connecting part 1061 extends through the through holes 1083 to threadedly couple with the lid 104. Accordingly, the obstructing part 1081 prevents the threaded connecting part 1061 from rotating.

Figure 5:
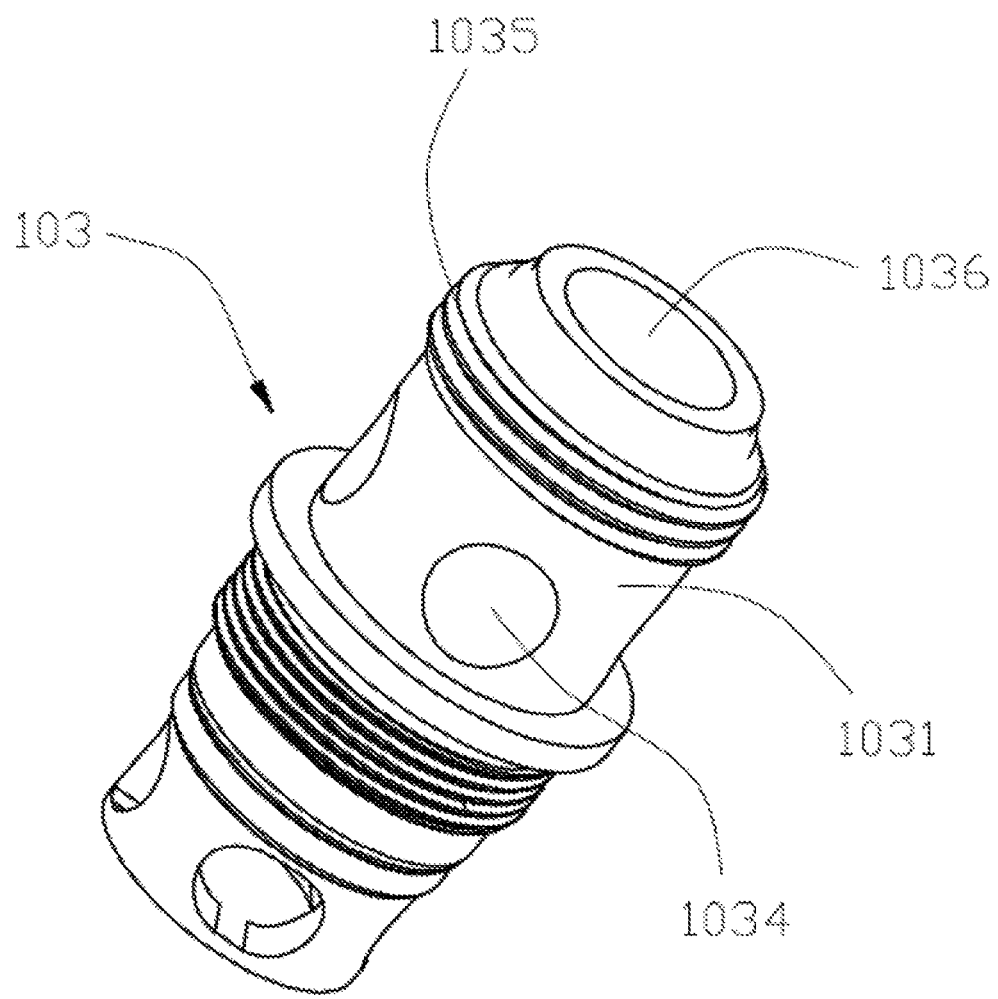
FIG. 5 is a perspective view of an atomizing core of the atomizer of FIG. 1.

Referring to FIGS. 1 and 5, the atomizing core 103 includes a main body 1031, a liquid absorbing body 1033 arranged in the main body 1031, and a heating element 1032. The main body 1031 defines at least one liquid inlet 1034, and the liquid blocking cover 106 can open or close the at least one liquid inlet 1034. The main body 1031 further includes a plurality of threads 1035, so that the atomizing core 103 can be detachably assembled in the housing assembly 101. The atomizing core 103 defines an air outlet 1036 at the top in communication with the air pipe 107. An electrode assembly 109 is provided at a bottom part of the housing assembly 101, and is electrically connected with the heating element 1032. The electrode assembly 109 is configured for connecting with a power supply. After detaching the electrode assembly 109, the atomizing core 103 can be replaced.

Quite usefully, the heating element 1032 is oriented along an axial direction of the housing assembly 101, and the liquid absorbing body 1033 wraps around the heating element 1032. The heating element 1032 may be a spiral heating wire, and the liquid absorbing body 1033 may be made of porous ceramic, fiber cotton, or glass fiber material. The liquid absorbing body 1033 defines a central through hole, and the heating element 1032 is arranged in the central through hole, and on the inner surface of the liquid absorbing body 1033. Tobacco liquid flowed in from the liquid inlet 1034 is absorbed by the liquid absorbing body 1033, and is then heated to form aerosol by the heating element 1032.

Figure 6:
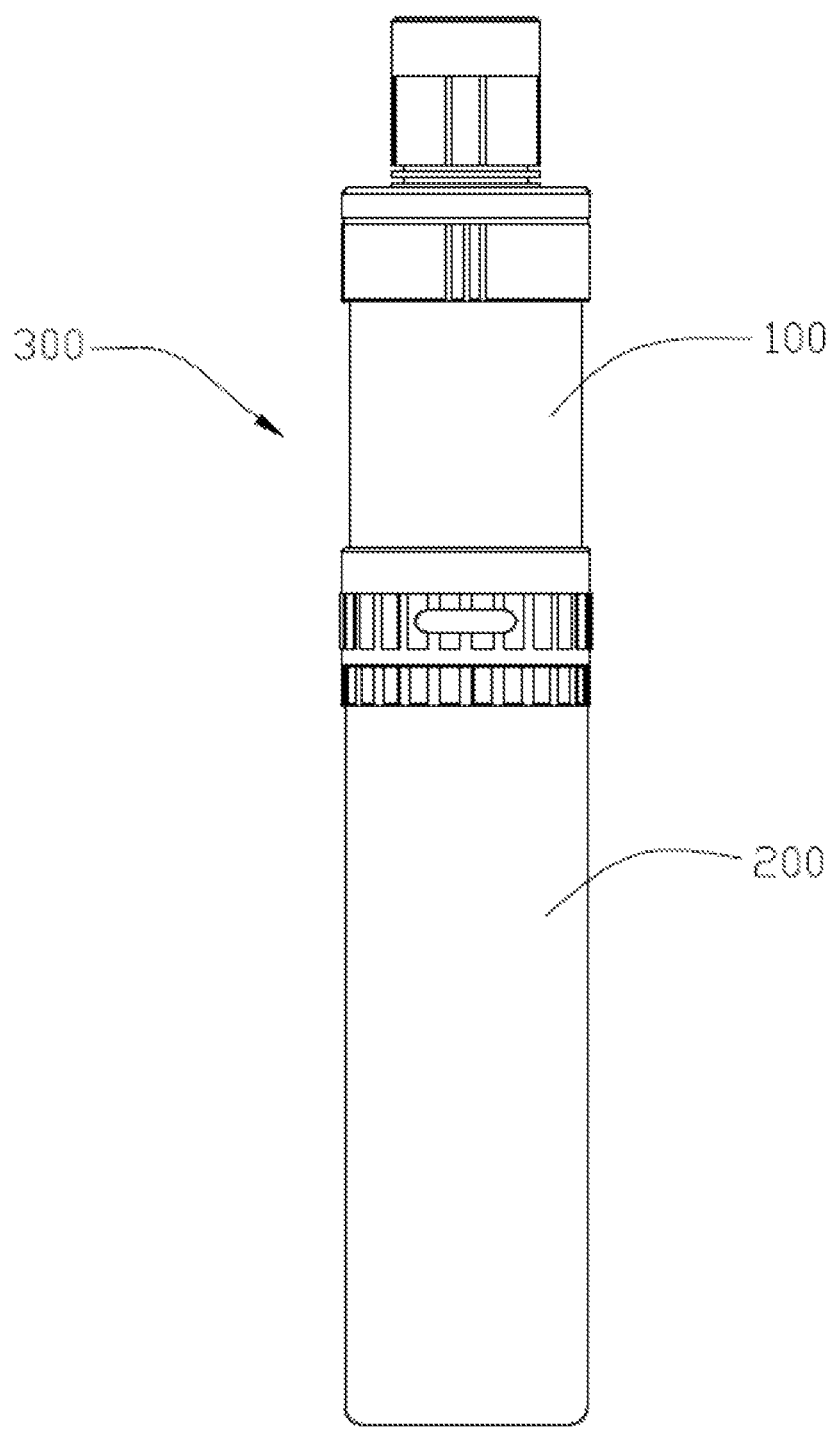
FIG. 6 is a side view of an electronic cigarette according to another embodiment.

Referring to FIG. 6, an electronic cigarette 300 is shown. The electronic cigarette 300 includes a power supply 200, and the atomizer 100 connected with the power supply 200. The power supply 200 includes a lithium battery. The power supply 200 is configured for supplying the atomizer 100 power.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer, comprising:
a housing assembly defining a liquid chamber configured for storing tobacco liquid;
an atomizing core arranged in the housing assembly, the atomizing core being configured for atomizing the tobacco liquid;
a lid being disposed at one end of the housing assembly, the lid being configured for sealing the liquid chamber, the lid being detachable from the housing assembly so that tobacco liquid can be filled into the liquid chamber;
a liquid blocking cover movably arranged in the housing assembly and defining a space therein to receive the atomizing core, the liquid blocking cover being detachably connected with the lid; and an elastic element elastically abutting against the liquid blocking cover; wherein when the lid is connected with the liquid blocking cover, the lid is capable of driving the liquid blocking cover to move to a first position where the tobacco liquid in the liquid chamber can flow to the atomizing core; when the lid is detached from the liquid blocking cover, the liquid blocking cover is driven by the elastic element to a second position where the atomizing core is completely covered by the liquid blocking cover to be located inside the space of the liquid blocking cover and spatially isolated from the liquid chamber.

2. The atomizer according to claim 1, wherein the lid is rotatably connected with the housing assembly, and the lid and the liquid blocking cover are threadedly coupled with each other.

3. The atomizer according to claim 2, further comprising a mouthpiece arranged on the lid, and an air pipe between the mouthpiece and the atomizing core, wherein the liquid blocking cover nest the air pipe, and is slidable along an axial direction of the air pipe.

4. The atomizer according to claim 3, wherein the air pipe comprises an obstructing part, and the obstructing part is configured for preventing the liquid blocking cover from rotating when the lid is threadedly connected with the liquid blocking cover.

5. The atomizer according to claim 3, wherein the liquid blocking cover comprises a nesting part, an isolating part, and a threaded connecting part; the nesting part sleeves the air pipe, the isolating part receives the atomizing core, and the threaded connecting part is configured for connecting with the lid.

6. The atomizer according to claim 1, wherein the liquid blocking cover and the housing assembly cooperatively define the liquid chamber, and the liquid blocking cover further defines a liquid filling opening.

7. The atomizer according to claim 1, wherein the atomizing core comprises a main body, a liquid absorbing body arranged in the main body, and a heating element in the main body; the main body defines at least one liquid inlet, and the liquid blocking cover is capable of opening or closing the at least one liquid inlet.

8. The atomizer according to claim 7, wherein the heating element is oriented along an axial direction of the housing assembly, and the liquid absorbing body wraps around the heating element.

9. The atomizer according to claim 8, wherein the heating element is a spiral heating wire, and the liquid absorbing body is made of material selected from a group consisting of porous ceramic, fiber cotton, and glass fiber material.

10. An electronic cigarette, comprising:
the atomizer according to claim 1; and
a power supply configured for supplying the atomizer power.

11. The atomizer according to claim 1, wherein the liquid blocking cover is closer to the one end of the housing assembly in the first position thereof than in the second position thereof.

12. The atomizer according to claim 5, wherein the threaded connecting part is divided into two pieces, and the obstructing part defines two through holes, so that the two pieces of the threaded connecting part extends through the through holes to threadedly couple with the lid.

* * * * *